United States Patent
Tian et al.

(10) Patent No.: US 7,247,712 B2
(45) Date of Patent: Jul. 24, 2007

(54) COMPLEX OF HEPATITIS B VIRUS-SPECIFIC ANTIGENIC PEPTIDES ASSOCIATED WITH HEAT SHOCK PROTEINS AND THE APPLICATION THEREOF

(75) Inventors: Bo Tian, Beijing (CN); Songdong Meng, Beijing (CN); George F. Gao, Beijing (CN)

(73) Assignee: Institute of Microbiology, Chinese Academy of Sciences, Beijing (CN)

( * ) Notice: Subject to any disclaimer, the term of this patent is extended or adjusted under 35 U.S.C. 154(b) by 528 days.

(21) Appl. No.: 10/344,502

(22) PCT Filed: Feb. 27, 2001

(86) PCT No.: PCT/CN01/00295

§ 371 (c)(1),
(2), (4) Date: Jul. 28, 2003

(87) PCT Pub. No.: WO02/14370

PCT Pub. Date: Feb. 21, 2002

(65) Prior Publication Data

US 2004/0047879 A1    Mar. 11, 2004

(30) Foreign Application Priority Data

Aug. 11, 2000  (CN) .................... 00 1 21270
Feb. 20, 2001  (CN) .................... 01 1 04060

(51) Int. Cl.
*A61K 38/10*    (2006.01)

(52) U.S. Cl. .................... 530/402; 424/218.1
(58) Field of Classification Search ............ None
See application file for complete search history.

(56) References Cited

U.S. PATENT DOCUMENTS 6,030,618 A *  2/2000  Srivastava .......... 424/184.1
6,921,534 B2 *  7/2005  Mizzen et al. ........ 424/189.1

FOREIGN PATENT DOCUMENTS

WO    WO 99/45954    *  9/1999

OTHER PUBLICATIONS

Engler et al., Peptide vaccines against hepatitis B virus: from animal model to human studies. (2001) Molecular Immunology 38, p. 457-465.*

(Continued)

*Primary Examiner*—Bruce R. Campell
*Assistant Examiner*—Agnieszka Boesen
(74) *Attorney, Agent, or Firm*—Knobbe, Martens, Olson & Bear, LLP (57) ABSTRACT

The present invention provides a kind of HBV-antigen bound to heat shock proteins (hsps) which comprises core antigen, surface antigen and polymerase antigen. The present invention also provides a complex of HBV antigen bound to heat shock protein gp96 and hsp78, as well as a method for preparing the complex. The complex includes a complex of gp96 and hsp78 non-covalently bound to antigenic polypeptide, as well as a fusion protein of both which results from covalent binding. Such complex can be used to prepare therapeutic vaccine for treating hepatitis B and primary hepatocellular carcinoma.

9 Claims, 1 Drawing Sheet

OTHER PUBLICATIONS

Peng et al., Novel vaccines for the treatment of hronic HBV infection based on mycobacterial heat shock protein 70. Vaccine (2006) vol. 24, p. 887-896.*

Liu et al., Recombinant Adeno-associated virus expressing human Papillomavirus type 16E7 peptide DNA fused with heat shock protein DNA as a potential vaccine for cervical cancer. Journal of virology. (2000) p. 2888-2894.*

Kregel. Heat shock proteins: modifying factors in physiological stress responses and acquired thermotolerance. (2002) Journal of Applied Physiology, vol. 92. p. 2177-2186.*

Belli F. et al. 2002 Vaccination of Metastitic Melanoma Patients with Autologous Tumor-Derived Heat Shock Protein $gp^{96}$-Peptide Complexes: Clinical and Immunologic Findings, *Journal of Clinical Oncology*, 20:4169-4180.

Tamura, Y. et al., 1997 Immunotherapy of Tumors with Autologous Tumor-Derived Heat Shock Protein Preparations, *Science*, 278:117-120.

Yedavelli S.P.K. et al., 1999 Preventive and Therapeutic Effect of Tumor Derived Heat Shock Protein, $gp^{96}$, in an Experimental Prostate Cancer Model, *International Journal of Molecular Medicine* 4:243-248.

* cited by examiner

Fig.1

US 7,247,712 B2

SEQUENCE LISTING

```
<160> NUMBER OF SEQ ID NOS: 12

<210> SEQ ID NO 1
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 1

Tyr Val Asn Thr Asn Met Gly
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 2

Tyr Val Asn Val Asn Met Gly
1               5
```

```
<210> SEQ ID NO 3
<211> LENGTH: 29
<212> TYPE: DNA
<213> ORGANISM: Artificial Sequence
<220> FEATURE:
<223> OTHER INFORMATION: synthetic primer

<400> SEQUENCE: 3
ccggatccga acttgatgtg gatggtaca                                29

<210> SEQ ID NO 4
<211> LENGTH: 32
<212> TYPE: DNA
<213> ORGANISM: Artificial Sequence
<220> FEATURE:
<223> OTHER INFORMATION: synthetic primer

<400> SEQUENCE: 4
ccgagctccc aaatggtgag agtataattt ac                            32

<210> SEQ ID NO 5
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 5

Tyr Val Asn Thr Asn Met Gly Leu Lys
1               5

<210> SEQ ID NO 6
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 6

Ser Thr Leu Pro Glu Thr Thr Val Val Arg Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 7

Phe Leu Pro Ser Asp Phe Phe Pro Ser Val
1               5                   10

<210> SEQ ID NO 8
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 8

Ile Pro Ile Pro Ser Ser Trp Ala Phe
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 9

Trp Leu Ser Leu Leu Val Pro Phe Val
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 10

Phe Leu Leu Ser Leu Gly Ile His Leu
1               5

<210> SEQ ID NO 11
<211> LENGTH: 33
<212> TYPE: DNA
<213> ORGANISM: Artificial Sequence
<220> FEATURE:
<223> OTHER INFORMATION: synthetic primer

<400> SEQUENCE: 11
ggggatccat agaagttcac tgtggtggcg gcg                              33

<210> SEQ ID NO 12
<211> LENGTH: 32
<212> TYPE: DNA
<213> ORGANISM: Artificial Sequence
<220> FEATURE:
<223> OTHER INFORMATION: synthetic primer

<400> SEQUENCE: 12
gggtcgacct actactcatc tttttctgat gt                               32
```

COMPLEX OF HEPATITIS B VIRUS-SPECIFIC ANTIGENIC PEPTIDES ASSOCIATED WITH HEAT SHOCK PROTEINS AND THE APPLICATION THEREOF

RELATED APPLICATIONS

This is the U.S. national phase under 35 U.S.C. 371 of International Application PCT/CN01/00295, filed Feb. 27, 2001, designating the US and published in Chinese, which claims priority to Chinese Patent Application 00121270.2, filed Aug. 11, 2000, and Chinese Patent Application 01104060.2, filed Feb. 20, 2001.

FIELD OF THE ART

The present invention relates to a complex of HBV antigenic polypeptide bound to heat shock protein gp96 and hsp78, as well as the application thereof.

BACKGROUND OF THE ART

Heat shock protein (hsp) gp96 (glycoprotein 96), also called as grp94 (glucose-regulated protein 94), is a member of hsp90 family which located on endoplasmic reticulum (ER) membrane of cells, the protein has about 96 KDa of molecuar weight and plays an important role in cellular protein folding and transportation. Recent studies have showed that gp96 is also expressed on the surface of some tumor cells. Gp96 possesses two conserved domains, the C-terminal is a polypeptide-binding domain which can bind a variety of polypeptides with 5-25 amino acids, and the N-terminal is a ATP-binding domain with ATPase activity. Heat shock protein hsp78, a member of hsp70 family in cytoplasma, has about 78 KDa of molecular weight and plays an important role in cellular protein folding and transportation. Hsp78 can bind to a variety of short peptides as molecular chaperone, it has two functional domains: the N-terminal domain with ATPase activity and the C-terminal domain which can bind to polypeptide substrate.

Recent studies demonstrated that immunization with gp96 and hsp78 purified from tumor tissues or cells infected by virus could elicit a specific immunological rejection response against the tumors or viruses. A further study showed that gp96 and hsp78 can bind to all peptide libraries generated in the cells including antigenic polypeptides, this specific immunological response is based on the polypeptides bound to gp96 and hsp78 not the heat shock protein itself, gp96 and hsp78 from tumor tissues or cells infected by virus normally bind to tumor or virus specific polypeptides, gp96 and hsp78 can present the antigenic ploypeptides bound by them to major histocompatibility complex (MHC) molecules and activate cytotoxic T lymphocyte (CTL) to elicit cell immunological response generated by organism. Since gp96 and hsp78 play an important role in antigen presentation in the cells, gp96-ploypeptide complex and hsp78-polypeptide complex can be used to prevent autogenous tumors and some infectious diseases.

Pramod K. Srivastava from University of New York, USA, applied for 6 patents (U.S. Pat. Nos. 6,017,544, 6,017,540, 6,007,821, 5,837,251 and 5,830,464) in USA based on his studies. These patents mainly relate to the use of a complex of heat shock protein (hsp) non-covalently bound to antigen molecular for treating primary and transferred tumors as well as infectious diseases, and activating immunological response generated by organism, wherein the antigen moleculars include the esoteric polypeptides bound to hsp, and also include exoteric antigens or immunogenic fragments that can form complex with hsp in vitro. Hsp mainly comprises hsp70, hsp90 and gp96 protein.

It has been demonstrated that gp96 and hsp78 can bind antigenic polypeptides such as antigenic peptide of vesicular stomatitis virus, ovalbumin antigenic epitope peptide restricted by mouse H-2K$^b$ and an L$^d$-restricted CTL epitope peptide of a mouse leukemia. Up to now, however, no antigenic ploypeptides bound to hsps have yet been identified in patients tissues infected by virus.

It is estimated that about 350 million individuals worldwide have been infected by HBV, and in China alone the number is about 120 million. HBV is the leading cause of chronic hepatitis, cirrhosis and liver cancer, so it is a kind of infectious diseases that severely disserve the life health of Chinese. The probability of liver cancer developing from hepatitis B is also very high. The HBcAg-positive hepatocytes accout for 62.5% in total HCC cells and 29.2% in the totally adjacent liver cells. Cell immunological response elicited by CTL is a major pathway to clear virus and cure hepatitis B. In the patients infected by hepatitis B virus, the HBV antigenic ploypeptide is presented to MHC I molecular after process, and activates specific CTL to elicit cell immunological response. Now, some CTL epitopes on the HBV core protein have been identified, including HLA-A2 restricted HBcAg18-27, HLA-A11 restricted HBcAg88-96 and like. Therefore, it is very important to develop a novel drug for the prevention and treatment of HBV associated hepatitis and primary hepatocellular carcinomas, especially a drug that can elicit actively CTL immunological response generated by organism.

SUMMARY OF THE INVENTION

One object of the invention is to provide a complex of a HBV antigenic molecule bound to gp96 and hsp78. The HBV antigen can be the following amino acid sequences respectively, such as "YVNTNMG" or a variant thereof (derived from core protein of HBV 88-94); "YVNTNMGLK" or a variant thereof (derived from core protein of HBV 88-96); "STLPETTVVRR" or a variant thereof (derived from core protein of HBV 141-151); "FLPSDFFPSV" or a variant thereof (derived from core protein of HBV 18-27); "IPIPSSWAF" or a variant thereof (derived from surface protein of HBV 313-321); "WLSLLVPFV" or a variant thereof (derived from surface protein of HBV 355-363); and "FLLSLGIHL" or a variant thereof (derived from polymerase of HBV 575-583).

The variant sequence is obtained from HBV by one or more replacment, deletion, increment of amino acids or modification of side chains, and has the antigenic sequence of the HBV.

The complex of the present invention consists of the heat shock protein non-covalently and covalently bound to polypeptide.

A further object of the invention is to provide a method for preparing a complex of HBV antigenic polypeptide and heat shock protein gp96 and hsp78 as described above of the present invention.

A still further object of the invention is to provide the application of these complexes of the invention for preparing the drug that can treat hepatitis B and primary hepatocellular carcinomas.

We isolated for the first time a specific 7-mer peptide in the polypeptide bound to heat shock protein gp96 from six human liver cancer tissue infected by HBV and found the 7-mer peptide has the amino acids sequence: "YVNTNMG or YVNVNMG" by sequencing. We searched the GenBank with a BLAST search using the National Center for Biotechnology Information Website and found that the peptide were derived from amino acid residues 88-94 of the core protein of HBV. The complex of gp96-7 mer peptide can be reconstituted in vitro with the synthesized peptide sequence and expressed gp96 protein in vitro. Mice were immunized with 7-mer peptide or gp96-7 mer peptide complex. The results showed that both them can elicit the specific CTL response in mice. Immunization with the gp96-7 mer peptide resulted in >200-fold immunogenicity in comparison to 7-mer peptide only controls. The experiment result showed that the gp96-7 mer peptide complex can be developed as a novel drug for treatment of hepatitis B and primary hepatocellular carcinoma.

The artificially synthesized 7-mer peptide "YVNTNMG, or YVNVNMG" and 7-mer peptide with N-terminal labeled by fluorescein were used to constitute the reaction system of gp96 protein bound to 7-mer peptide labled by fluorescein. The formula is presented as follows:

$$G + P \underset{k_2}{\overset{k_1}{\rightleftharpoons}} GP,$$

wherein G is gp96 protein, P is 7-mer peptide, GP is the complex of gp96 protein-7 mer peptide, and $k_1$ and $k_2$ represent the forward and the reverse rate constants, respectively. The equilibrium constant (k) of the reaction is given by the following relationship $$k = k_1/k_2 = [GP]/[G][P]$$

wherein [GP], [G] and [P] is the concentration of the reaction product GP and substrate G, P, respectively. In order to find the optimum reaction condition, we assessed several impact factors of the reaction system such as optimum temperature, salt concentration, pH value, additive, catalyst, the optimum reaction concentration rate of gp96 protein and 7-mer peptide and like, and determined the reaction constant.

Synthesis of the gp96 protein-7 mer complex in vitro is performed under the optimum reaction system condition.

The present invention also provides a method for preparing the complex HBV antigen 7-mer peptide and heat shock protein gp96 comprising the gp96 protein and the HBV antigen are incubated for 10 minutes to 30 minutes at 37-39° C. in a low-salt buffer with a maximum concentration of 100 mmol/L comprising 5-10% (v/v) glycerol, wherein the concentration of the gp96 protein is 0.1-0.15 µmol/L and the concentration of HBV antigen is 2.5-3.5 µmol/L.

In the method of the present invention, the temperature is preferably 37° C., and the reaction time is preferably 15 minutes.

In the method of the present invention, the concentration of the gp96 is preferably 0.12 µmol/L, and the concentration of the HBV antigen is preferably 3.0 µmol/L.

The present invention also provides a fusion protein formed by covalent bind of HBV antigen 7-mer peptide and heat shock protein gp96. The sequence of nucleic acid corresponding to the peptide was synthesized artificially, and the sequence was ligated with the 5'-terminal of the gp96 gene by conventional methods of molecular biology and then expressed in the E. coli. For example, after the restriction site of Bgl II is introduced into the 7-mer peptide, the nucleic acid sequence is ligated with 5'-terminal of gp96 gene by $T_4$ ligase, the restriction sites of two restriction endonucleases BamHI and SacI are introduced into the 5'-terminal and 3'-terminal of the ligation product respectively, then ligated into the expression vector pET30a and expressed in the E. coli. The expression product is the fusion protein of gp96 and 7-mer peptide.

Immunization with gp96 protein-7 mer complex of the invention including the complex formed by the above gp96 non-covalently bound to the 7-mer peptide in vitro and the fusion protein formed by the above gp96 covalently bound to the 7-mer peptide can be performed using any known immunological manner, for example, subcutaneous injection, intradermal injection, intraperitoneal injection and like. The dosage of immunization with gp96 protein-7 mer peptide complex can be, for example, 0.01 nmol, 0.05 nmol, 0.10 nmol and 0.50 nmol. When the immunization is performed only with 7-mer peptide, the dosage of immunization can be 0.2 nmol, 2 nmol, 20 nmol.

Any known adjuvant, such as Freund's adjuvant, chromium alum and like can be used or not when immunization is performed with gp96 protein-7 mer peptide complex.

A 9-mer peptide, "YVNTNMGLK", was also synthesized by our laboratory. A gp96 protein-9 mer peptide complex was synthesized according to the above optimum reaction system in vitro. Immunization can be performed using any known immunological manner, for example, subcutaneous injection, intraderma injection, intraperitonea injection and like. The dosage of immunization with gp96 protein-9 mer peptide complex can be, for example, 0.01 nmol, 0.05 nmol, 0.10 nmol and 0.50 nmol. When the immunization is performed only with 9-mer peptide, the dosage of immunization can be 0.2 nmol, 2 nmol, 20 nmol. Any known adjuvant, such as Freund's adjuvant, chromium alum and like can be used or not when immunization is performed. Both of the gp96-9 peptide complex and the 9-mer peptide can elicit the specific cytotoxic T lymphocytes (CTL) response in mice after immunization. The immunogenicity of the gp96-9 mer peptide is >300-fold in comparison to 9-mer peptide only controls. The experiment results showed that the gp96-9 mer peptide complex can be developed as a novel drug for treatment of hepatitis B and primary hepatocellular carcinoma.

In addition, we also synthesized 11-mer peptide "STLPETTVVRR"; 10-mer peptide "FLPSDFFPSV"; 9-mer peptide "IPIPSSWAF"; 9-mer peptide "WLSLLVPFV", and 9-mer peptide, "FLLSLGIHL". A gp96 protein-polypeptide complex is synthesized according to the above optimum reaction system in vitro. Immunization can be performed using any known immunological manner respectively, for example, subcutaneous injection, intraderma injection, intraperitonea injection and like. The dosage of immunization with gp96 protein-polypeptide complex can be, for example, 0.01 nmol, 0.05 nmol, 0.10 nmol and 0.50 nmol. When the immunization is performed only with polypeptide, the dosage of immunization can be 0.2 nmol, 2 nmol, 20 nmol. Any known adjuvant, such as Freund's adjuvant, chromium alum and like can be used or not when immunization is performed. Both of the gp96-polypeptide complex and the polypeptide can elicit the specific cytotoxic T lymphocyte (CTL) response in mice after immunization. The immunogenicity of the gp96-polypeptide complex is >150-fold in comparison to peptide only controls. The experiment results showed that the gp96-polypeptide complex can be developed as a novel drug for treatment of hepatitis B and primary hepatocellular carcinoma.

According to the optimum reaction system, we synthesized hsp78 protein-polypeptide complexes using the above synthesized multi-peptides including "YVNTNMG"; "YVNTNMGLK"; "STLPETTVVRR"; "FLPSDFFPSV"; "IPIPSSWAF"; "WLSLLVPFV"; "FLLSLGIHL". Immunization can be performed using any known immunological manner respectively, for example, subcutaneous injection, intraderma injection, intraperitonea injection and like. The dosage of immunization with hsp78 protein-polypeptide complex can be, for example, 0.01 nmol, 0.05 nmol, 0.10 nmol and 0.50 nmol. When the immunization is performed only with 7-mer peptide, the dosage of immunization can be 0.2 nmol, 2 nmol, 20 nmol. Any known adjuvant, such as Freund's adjuvant, chromium alum and like can be used or not when immunization is performed. Both of the hsp78-polypeptide complex and the polypeptides can elicit the specific cytotoxic T lymphocyte (CTL) response in mice after immunization. The immunogenicity of the hsp78-polypeptide is >150-fold in comparison to polypeptides only controls. The experiment result showed that the hsp78-polypeptide complex can be developed as a novel drug for treatment of hepatitis B and primary hepatocellular carcinoma.

DETAILED DESCRIPTION OF THE PREFERRED EMBODIMENTS

EXAMPLE

Example 1

Figure 1:
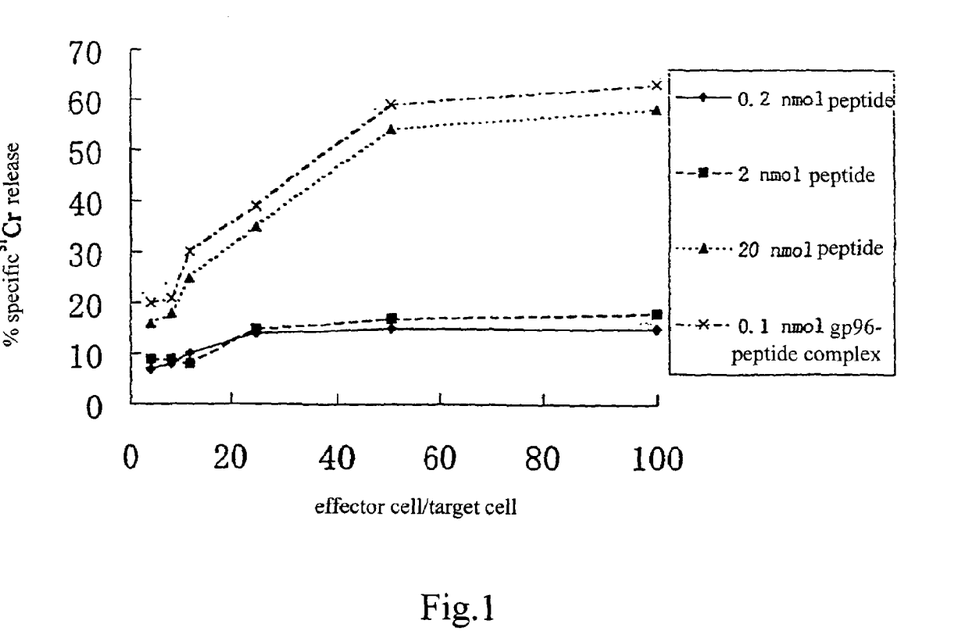
FIG. 1. Specific CTL response of BALB/cJ(H-$2^d$) mice after immunized with 7-mer peptied and gp96-7 mer peptide complex seven days. The lysis percentage of effector cells to specific target cells was measurated in a standard 4-h $^{51}$Cr release assay. The lysis percent rate of the figure is the mean percentage of 10 mice.

Purification of gp96 Protein from Human Liver Tissues

Three tumor tissues infected by HBV and an uninfected healthy normal tissue were homogenized and then centrifuged. The supernatant was precipitated with 50%-70% ammonium sulphate. The affinity chromatography was performed using ConA Sepharose (Pharmacia Co.,) after the precipitation was solubilized, the bound protein was eluted with 10% α-methylglucoside, and the eluent was loaded into the POROS 20QE (PE Co., BioCAD perfusion system) to perform anion chromatography. Using the three-step purification procedures, the gp96 protein of over 95% purity was obtained. The gp96 protein was identified by Western blotting using gp96/grp94 monoclonal antibody (NeoMarkers, Co.,). The purify of the gp96 protein was identified by SDS-PAGE, silver staining and reverse-phase HPLC.

Example 2

Separation of the Non-Covalently Bound Peptide from gp96 Protein

The trifluoroacetic acid (TFA) was added to the purified gp96 protein to obtain a final concentration of 0.2% TFA (pH is about 2.0), and then separated the polypeptide by ultra-filtration (molecular mass cutoff 10 KDa, Pall Filtron Co.,).

The polypeptides mixture was analyzed by MALDI-TOF mass spectrometry (PE Co., Voyager-DE system). The molecular weight of the polypeptides is mainly between 600 Da and 1100 Da.

Exampe 3

Reverse-Phase HPLC Analysis of Polypeptide

The polypeptides mixture was solubilized in solution A (0.065% TFA, 2% acetonitrile) after freeze-drying, and then loaded on C18 reverse-phase column (Sephasil peptide C18; 5 nm particle size; 4.6×250 nm, Pharmacia Co.,). The gradient elution was performed by using 0-65% solution B (0.05% TFA, 100% acetonitrile) with a flow rate of 1 ml/min and detected by 214 nm wavelength. Compared the HPLC map of the liver cancer tissues and the normal tissue, we found that a peptide peak presented in the three liver cancer tissues rather than the normal tissue.

Example 4

Microsequencing and Sequence Analysis of Polypeptides

The specific peptide peak was collected and the purity was identified by MALDI-TOF mass spectrometry (PE Co., Voyager-DE system), and there was one single peak of 798 Da. Microsequencing of the polypeptide (Procise™ 491 protein sequencer, PE Co.) showed that all three samples from liver tissues had the same sequence: "YVNTNMG" (SEQ. ID NO: 1), or "YVNVNMG" (SEQ. ID NO: 2). We searched the protein Data Bank on PubMed net (ncbi.nlm.nih.gov) for the sequence and found that it was located at position 88-94 in core protein of HBV.

Example 5

Cloning of gp96 Gene

The total RNA was extracted from 0.5 ml human blood which was heated at 42° C. for 2 hours with guanidine isothiocyanate using RNA Isolation Kit (Catrimox-14™ RNA Isolation Kit Ver. 2.11) of TaKaRa Biotechnology (Dalian). The steps were performed according to the description of the kit.

The human gp96 gene was cloned by reverse transcription-polymerase chain reaction (RT-PCR) using the RT-PCR Kit (TaKaRa RNA LA PCR™ Kit AMV Ver. 1.1) of TaKaRa Biotechnology (Dalian) Inc. The steps were performed according to the description of the kit. The primers as following:

```
Primer 1: 5'-CCGGATCCGAACTTGATGTGGATGGTACA-3'

Primer 2: 5'-CCGAGCTCCCAAATGGTGAGAGTATAATTTAC-3'
```

The reaction condition of PCR as following: 94° C. 4 minutes; and 30 cycles of 94° C. 50 seconds, 55° C. 50 seconds, 72° C. 3 minutes, and ended with 5 minutes at 72° C.

The product of PCR was about 2.4 Kd and the restriction sites of two restriction endonucleases BamHI and SacI were introduced into the 5'-terminal and the 3'-terminal of the fragment artificially. Sequenced the amplified fragment and found that the gp96 gene contains 2343 bp, the base sequence is identical with the sequence reported in the reference (Maki, R G, et al. GeneBank, No: 003299).

Example 6

Expression and Purification of the gp96 Gene and the Ligation Fragment of gp96 Gene and HBV Antigenic Polypeptide Nucleic Acid in *E. coli*

After PCR amplification, the resulting fragment was digested by BamH1 and Sac1 and ligated into the expression vector pET30a(+), and then transformed into BL21. At the same time, the DNA fragments corresponding to the following polypeptides were synthesized artificially: "YVNT-NMG" (SEQ ID NO: 1), "YVNTNMGLK" (SEQ ID NO: 5), "STLPETTVVRR" (SEQ ID NO 6), "FLPSDFFPSV" (SEQ ID NO 7), "IPIPSSWAF" (SEQ ID NO 8), "WLSLLVPFV" (SEQ ID NO: 9), "FLLSLGIHL" (SEQ ID NO: 10). We also introduced the restriction site of Bgl II into both terminals of the DNA fragment and then inserted the DNA fragments encoding the polypeptides into the Pet30a (+) plasmid containing the gp96 gene.

The constructed expression vector was induced with 1 mM isopropyl-β-thiogalactoside (IPTG) for 4 hrs and then expressed. The expressed product was electrophoresed with 10% SDS-PAGE and then stained with Coomassie brilliant blue. The molecular weight of the expressed product is about 100 Kda corresponding to the theoretical value essentially.

The gp96 protein and the fusion protein of the gp96 protein and the HBV antigenic polypeptide were both purified by affinity chromatography using Ni-affinity chromatography column (Pharmacia Co.,) and anion-chromatography using POROS 20QE (PE Co., BioCAD infusion chromatography system). The purified protein was electrophoresed with 10% SDS-PAGE and then stained with sliver to determine the purify. The purity of the gp96 protein and the fusion protein thereof were >95%. The expressed gp96 protein and the fusion protein of the gp96 protein and the HBV antigenic polypeptide were identified by Western blotting using gp96/grp94 monoclonal antibody (NeoMarkers Co.,).

Example 7

The Experiment Condition of Assembling the gp96 Protein and the Artificially Synthesized Polypeptide In Vitro The 7-mer peptide, "YVNTNMG" or "YVNVNMG" labeled by fluorescein was artificially synthesized (Sai baisheng Biotech Company). The gp96 protein and the polypeptides were assembled in vitro. A serial of experiments were performed as following to determine the optimum reaction condition:

Temperature experiment of reaction system: 55° C., 39° C., 37° C., 30° C., or 28° C.

Salt concentration experiment of reaction system: low salt buffer (20 mmol/L HEPES, pH7.9, 20, 100 or 500 mmol/L NaCl, 2 mmol/L MgCl$_2$); high salt buffer (20 mmol/L HEPES, pH7.9, 0.5, 1.0 or 2.2 mol/L NaCl, 2 mmol/L MgCl$_2$)

pH value experiment of reaction system: pH6.0, pH7.0, pH7.9 and pH9.0

Additive and catalyst of reaction system: 10 mmol/L ADP, 10 mmol/L ATP, and 10% (V/V) glycerol The optimum reaction concentration of the gp96 protein and the 7-mer peptide as well as the concentration rate thereof: the concentration of the 7-mer peptide in the reaction system is 0.5, 1.0, 1.5, 2.0, 2.5, 3.0, 3.5 μmol/L, respectively. the concentration of the gp96 protein in the reaction system is 0.06, 0.09, 0.12, 0.15, 0.18, 0.21 μmol/L. The reaction constant k was determined. The content of the gp96 protein was calculated by the following formula: $c=1.45A_{280}-0.74A_{260}$, wherein c is protein concentration, $A_{280}$ and $A_{260}$ represent light absorption value at a wavelength of 280 nm and 260 nm, respectively. The content of the 7-mer peptide labled by fluorescein was represented by the light absorption value at a wavelength of 378 nm. The unbound 7-mer peptide was removed completely by ultrafiltration (molecular mass cutoff 10 KDa, Pall Filtron Co.,) after the binding reaction. The content of the gp96 protein-7 mer peptide complex was represented by the light absorption value at a wavelength of 378 nm.

Example 8

The Construction of Optimum Reaction System of Assembling the gp96 Protein and Artificially Synthesized Polypeptid s In Vitro Using multi-component variance analysis, we determined the optimum reaction condition.

The 7-mer peptide "YVNTNMG" or "YVNVNMG" was synthesized artificially (Sai baisheng Biotech Company). We determined the optimum binding reaction system in vitro: 20 mmol/L HEPES, pH 7.9, 20 mmol/L NaCl, 2 mmol/L MgCl$_2$, 10% (V/V) glycerol, 3.0 μmol/L 7-mer peptide, and 0.12 μmol/L gp96 protein. Then, the mixture is incubated for 15 minutes at 37° C. The unbound polypeptides were removed completely by ultrafiltration (molecular mass cutoff 10 KDa, Pall Filtron Co.,). Results showed that gp96 binds 7-mer peptide with reasonably high affinity and the calculated equilibrium constant of the bingding reaction k is about 5-10.

Example 9

Stability Analysis of gp96 Protein-7 mer Peptide Complex

It was observed that gp96 protein-7 mer peptide complex assembled in vitro was unstable in PBS buffer at 4° C., -20° C., -70° C., and the gp96 protein tends to form dimer or polymer after stored 30 days by identifying with 10% SDS-PAGE and silver staining analysis. The complex was extremely stable in the form of freeze drying at 4° C., and the degradation rate of samples is lower than 5% after 90 days by detecting with 10% SDS-PAGE and silver staining as well as reverse-phase HPLC analysis.

Example 10

Immunization in Mice

BALB/cJ mice (H-2$^d$) 12-16 weeks old were used in this studies.

Sample was solubilized in 100 μl PBS and was injected subcutaneously in the neck back area of each mouse. Since it is not operated easily, we did not adopt intradermal injection although it needs lower dosage of immunization. Whereas intraperitoneal injection needs higher dosage of immunization to exert effect, about 0.5 nmol, so we did not adopt it.

The optimum immunization dosage used for gp96 protein-7 mer peptide complex is 0.1 nmol.

The immune effect of mice immunized twice, 7 days apart, is higher than that of mice immunized once.

The experiment of using adjuvant showed that Freund's incomplete adjuvant (FIA), Freund's complete adjuvant (FCA) and chromium alum did not enhance but decrease the immunogenicity of the gp96 protein-7 mer peptide complex. The phenomena is likely because adjuvant may destroy the structure of the gp96 protein-7 mer peptide complex. For 7-mer peptide, both of Freund's adjuvant and chromium alum can improve the immunological activity of it significantly, and the effect of Freund's adjuvant is better than chromium alum.

Therefore, we adopted the immunological manner of subcutaneous injection. The 7-mer peptide was dissolved in buffer (90% PBS, 10% DMSO/0.1% TFA) and gp96-7 mer peptide complex was dissolved in PBS buffer and then shaked severely for 1 minute before injection. For each mouse, the immunization dosage of 7-mer peptide was 0.2 nmol, 2 nmol and 20 nmol, respectively, the mice were immunized with peptide and Freund's after emulsion. The immunization dosage of gp96-7 mer peptide complex was 0.01 nmol, 0.05 nmol, 0.10 nmol and 0.50 nmol, respectively, the mice were immunized with subcutaneous injection in neck back area, and the second enhanced immunization was performed after one week from the first immunization, then cytotoxicity analysis was performed after 7 days. Each treatment group consisted of 10 mice.

Example 11

Cytotoxicity (CTL) Aanalysis

After 7 days, $3\times10^7$ spleen cells obtained from each mouse were suspended in culture medium comprising 10 mM HEPES buffer, $5\times10^{-5}$ M mercaptoethanol, antibiotics and 10% (V/V) FCS and cultured with irradiated (4500 Rad) B lymphocytes (3:1) stimulated by homogenous LPS and 1 μg/ml peptide in the complete medium at 37° C. After 6 days, spleen cells were collected and the standard 4-h $^{51}$Cr release assay was performed to test the cytotoxicity activity (see Kuhrober, A, et al. 1997. International Immunology, 9(8):1203-1212). In brief, the target cells were sensitized with 10 μg/ml peptide for 30 minutes at 37° C., and then various numbers of effctor cells in a final volume of 100 μl of complete culture medium. After incubation at 37° C. for 4 hours, the supernatant was harvested to determine the percentage of specific lysis.

$^{51}$Cr release assay showed that both 7-mer peptide and gp96-7 mer peptide complex can elicit the specific cytotoxic T lymphocytes in mice. Immunization with the gp96-7 mer peptide complex resulted in >200-fold immunogenicity in comparison to 7 mer peptide only. 0.1 nmol of gp96-7 mer peptide complex (10 μg/mouse) can elicit strong cell immune response and the percentage of lysis of target cells is over 60% determined by cytotoxicity. The results demonstrated that the gp96-7 mer peptide complex can be developed as a novel therapeutic drug against HBV infection and liver cancer infected with HBV.

Example 12

Determination of the Immunological Activity of Other gp96-Polypeptide Complexes

In addition to the above 7-mer peptide, we selected six HBV antigenic polypeptides assembled with gp96 in vitro and determined the immunological activity thereof. The six antigenic polypeptides are the followings: (1) core antigenic polypeptide "YVNTNMGLK" (located at 88-96 of amino acid sequence of core protein); (2) core antigenic polypeptide "STLPETTVVRR" (located at 141-151 of amino acid sequence of core protein); (3) core antigenic polypeptide "FLPSDFFPSV" (located at 18-27 of amino acid sequence of core protein); (4) surface antigenic polypeptide "IPIPSSWAF" (located at 313-321 of amino acid sequence of surface protein); (5) surface antigenic polypeptide "WLSLLVPFV" (located at 355-343 of amino acid sequence of surface protein); (6) polymerase antigenic polypeptide "FLLSLGIHL" (located at 575-583 of amino acid sequence of polymerase protein). These six polypeptides were synthesized respectively and bound to gp96 protein in vitro using the optimum reaction system described in example 8. All of six polypeptides can bind to gp96 with higher affinity. All the equilibrium constant K of binding reactions of six peptides and gp96 protein are over 5 by determining the equilibrium constant K of binding reactions.

The mice were immunized with the complexes of above six HBV antigenic polypeptides and gp96 protein as well as the fusion proteins of the above gp96 and the seven HBV antigenic polypeptides using the method described in example 10, and CTL analysis was performed using the method described in example 11. $^{51}$Cr release assay showed that all the six complexes of HBV antigenic polypeptides and gp96 protein can elicit the specific cytotoxic T lymphocytes in mice. Immunization with the complexes of six polypeptides and gp96 protein resulted in 150-300 fold immunogenicity in comparison to polypeptides only controls. 0.1 nmol of immunization dosage (10 μg/mouse) can elicit strong cell immune response and the percentage of lysis of target cells is between 60% and 85% by determining the cytotoxicity of the complexes formed by six polypeptides and gp96 protein.

The above results showed that the complexed assembled with gp96 protein and HBV antigenic polypeptides in vitro can be developed as a novel therapeutic drug against HBV infection and liver cancer infected with HBV. It is impossible to study the reconstitution in vitro and immunological activity of all HBV antigenic polypeptides in the present invention because of the limited experiment condition. However, the seven representative HBV core antigens, surface antigens as well as polymerase antigen were used in the invention and bound to gp96 in vitro to determine the immunological activity. A large number of experiments demonstrated that all the complexes formed by gp96 protein and these HBV antigenic polypeptides can elicit the strong immune response in mice. As a novel good adjuvant of HBV antigenic polypeptide, gp96 protein can be developed as a novel therapeutic vaccine. Thus, all of HBV antigenic polypeptides bound to gp96 protein as a novel vaccine should be involved in the present invention except the above seven HBV antigenic polypeptides.

Example 13

Cloning and Expression of Heat Shock Protein hsp78 Gene

The total RNA was extracted from 200 mg human liver cancer tissuse with guanidine isothiocyanate using RNA Isolation Kit (Catrimox-14TM RNA Isolation Kit Ver. 2.11) of TaKaRa Biotechnology (Dalian). The steps were performed according to the description of the kit.

The hsp78 gene of human hsp70 family was cloned by reverse transcription-polymerase chain reaction (RT-PCR)

using the RT-PCR Kit of TaKaRa Biotechnology (Dalian) Inc. The steps were performed according to the description of the kit.

The primers as following:

```
Primer 1: GG GGATCC ATG AAG TTC ACT GTG GTG GCG GCG

Primer 2: GG GTCGAC CTA CTA CTC ATC TTT TTC TGA TGT
```

The reaction condition of PCR as following: 94° C. 4 minutes; and 30 cycles of 94° C. 50 seconds, 55° C. 50 seconds, 72° C. 2 minutes, and ended with 5 minutes at 72° C.

The product of PCR was about 2.4 kb and the restriction sites of two restriction endonucleases BamHI and SalI were introduced into the 5'-terminal and the 3'-terminal of the fragment artificially. Sequenced the amplified fragment and found that the hsp78 gene contains 1965 bp, the base sequence is identical with the sequence reported in the reference (Mech. Ageing Dev. 1998, 104(2):149-158).

After PCR amplification, the resultant fragment was digested by BamHI and SalI and ligated into the expression vector pET30a(+), and then transformed into BL21. At the same time, the DNA fragments corresponding to the following polypeptides were synthesized artificially: "YVNTNMG", "YVNTNMGLK", "STLPETTVVRR", "FLPSDFFPSV", "IPIPSSWAF", "WLSLLVPFV", "FLLSLGIHL". We also introduced the restriction site of Bgl II into both terminals of the DNA fragment and then inserted the DNA fragments of the ploypeptides into the pET30a(+) plasmid containing the hsp78 gene.

The constructed expression vector was induced with 1 mM isopropyl-β-thiogalactoside (IPTG) for 4 hrs and then expressed. The expressed product was electrophoresed with 10% SDS-PAGE and then stained with Coomassie brilliant blue. The molecular weight of the expressed product is about 80 kDa corresponding to the theoretical value essentially.

The purification of the expressed product was performed by ADP-Agarose affinity chromatography (Sigma) and MonoQ (Pharmacia) anion chromatography. The purified protein was electrophoresed with 10% SDS-PAGE and then stained with Coomassie brilliant blue (about 5 μg of electrophoretic sample) to determine the purify. The purity of the protein was >95%. The expressed HSP78 protein and the fusion protein thereof were identified by Western blotting using hsp70 monoclonal antibody (Sigma).

Example 14

Determination of Immunogenicity of hsp78-Polypeptide Complexes

According to the described optimum reaction system in Example 8, hsp78 and seven polypeptides were assembled in vitro. The mice were immunized with the complexes synthesized in vitro and the fusion protein of hsp78 and seven polypeptides. The manner, dosage and procedure of immunization are the same as gp96 (see example 10). The method of cytotoxic (CTL) analysis is the same as gp96 (see example 11). $^{51}$Cr release assay showed that hsp78-7 mer peptide complex can elicit the specific cytotoxic T lymphocytes in mice. Immunization with the hsp78-7 mer peptide complex resulted in >150-fold immunogenicity in comparison to 7 mer peptide only controls. 0.1 nmol of immunization dosage (10 μg/mouse) can elicit strong cell immune response and the percentage of lysis of target cells is over 50% by determining the cytotoxicity. Our experiments demonstrated that the hsp78-7 mer peptide complex can be developed as a novel therapeutic drug against HBV infection and liver cancer infected with HBV.

What is claimed is:

1. A composition, comprising a complex of HBV antigen and a human heat shock protein gp96, wherein the HBV antigen consists of the amino acid sequence of: YVNTNMG (SEQ ID NO: 1).

2. A composition comprising complexes of (i) a human heat shock protein (HSP) molecule gp96, and (ii) variants of hepatitis B virus (HBV) antigen, wherein the HSP-HBV antigen complexes, when administered to an individual, induce or enhance an immune response against HBV infection, wherein the variants of HBV antigen are: SEQ ID NO: 1, SEQ ID NO: 2, SEQ ID NO: 5, SEQ ID NO: 6, SEQ ID NO: 7, SEQ ID NO: 8, SEQ ID NO: 9, and SEQ ID NO: 10.

3. The composition of claim 1, wherein the heat shock protein is non-covalently bound to the HBV antigen to form a fusion protein.

4. A method of making of the complex according to claims 1 or 2, comprising:
combining said heat shock protein having a concentration of between about 0.1 and about 0.15 µmol/L and the HBV antigen having a concentration of between about 2.5 and about 3.5 µmol/L to obtain a mixture;
incubating said mixture for about 10-30 minutes at a temperature of about 30-39° C. in a low salt buffer, said buffer having a concentration below about 100 mmol/L, wherein said buffer comprises glycerol in a concentration of about 5-10% (v/v).

5. The method of claim 4, wherein said incubating is performed for about 15 minutes at the temperature of about 37° C.

6. The method of claim 4, wherein the concentration of the heat shock protein is about 0.12 µmol/L, and the concentration of the HBV antigen is about 3.0 µmol/L.

7. The composition of claim 1, wherein the heat shock protein is covalently bound to the HBV antigen to form a fusion protein.

8. A composition comprising HBV antigens, wherein the antigens are: SEQ ID NO: 1, SEQ ID NO: 2, SEQ ID NO: 5, SEQ ID NO: 6, SEQ ID NO: 7, SEQ ID NO: 8, SEQ ID NO: 9, and SEQ ID NO: 10.

9. The composition according to claim 2, wherein the heat shock protein is non-covalently bound to the said variants or the heat shock protein is covalently bound to said variants to form a fusion protein.

* * * * *